US009068930B2

(12) United States Patent
Monaghan et al.

(10) Patent No.: US 9,068,930 B2
(45) Date of Patent: Jun. 30, 2015

(54) ANALYSIS DEVICE WITH TRANSDUCER STIFFENING ELEMENTS

(75) Inventors: Paul Brendan Monaghan, Sittingbourne (GB); Steven Andrew Ross, Ashford (GB); Timothy Joseph Nicholas Carter, Sheemess (GB)

(73) Assignee: VIVACTA LTD. (GB)

( * ) Notice: Subject to any disclaimer, the term of this patent is extended or adjusted under 35 U.S.C. 154(b) by 492 days.

(21) Appl. No.: 13/394,090

(22) PCT Filed: Sep. 1, 2010

(86) PCT No.: PCT/GB2010/051436
§ 371 (c)(1),
(2), (4) Date: May 14, 2012

(87) PCT Pub. No.: WO2011/027148
PCT Pub. Date: Mar. 10, 2011

(65) Prior Publication Data
US 2012/0220023 A1 Aug. 30, 2012

Related U.S. Application Data

(60) Provisional application No. 61/239,976, filed on Sep. 4, 2009.

(30) Foreign Application Priority Data

Sep. 3, 2009 (GB) .................................. 0915338.8

(51) Int. Cl.
*G01N 21/17* (2006.01)
*G01N 29/22* (2006.01)
(Continued)

(52) U.S. Cl.
CPC .......... *G01N 29/222* (2013.01); *G01N 21/8483* (2013.01); *G01N 25/48* (2013.01); *G01N 29/022* (2013.01); *G01N 2291/0255* (2013.01); *G01N 2291/0256* (2013.01)

(58) Field of Classification Search
CPC ....... G01N 21/17; G01N 25/48; G01N 29/02; G01N 29/24
USPC ................................................. 422/68.1, 400
See application file for complete search history.

(56) References Cited

U.S. PATENT DOCUMENTS

| 4,448,525 A | 5/1984 | Mikoshiba et al. |
| 5,622,868 A * | 4/1997 | Clarke et al. .................. 436/147 |
| 2001/0046107 A1 | 11/2001 | Irie et al. |

FOREIGN PATENT DOCUMENTS

| CN | 1318837 A1 | 2/2001 |
| EP | 1959512 A | 8/2008 |

(Continued)

OTHER PUBLICATIONS

International Search Report (ISR) and Written Opinion issued in the International Application No. PCT/GB2010/051436, Nov. 30, 2010.
(Continued)

*Primary Examiner* — Sally Merkling
(74) *Attorney, Agent, or Firm* — Wood, Phillips, Katz, Clark & Mortimer

(57) ABSTRACT

Disclosed herein is an analysis device for use with an external testing apparatus to detect the presence of an analyte in a test sample. The device comprises a transducer formed of a layer of pyroelectric or piezoelectric material sandwiched between first and second electrode layers, the transducer being arranged to produce an electrical voltage across the electrode layers in response to heating or straining of the pyroelectric or piezoelectric material layer. The device also comprises first and second stiffening elements for the transducer, the transducer being sandwiched between the stiffening elements. Each of the stiffening elements defines a planar surface for maintaining the transducer in a flat condition. Each of the stiffening elements exposes a portion of a respective electrode layer of the transducer for electrically connecting the transducer to the external text apparatus. The exposed portions are laterally offset from each other such that the exposed portions are each supported across the whole of their area by the stiffening element on the opposite side of the transducer. It has been found that such an arrangement may reduce noise caused by environmental effects.

20 Claims, 3 Drawing Sheets

(51) Int. Cl.
*G01N 21/84* (2006.01)
*G01N 25/48* (2006.01)
*G01N 29/02* (2006.01)

(56) References Cited

FOREIGN PATENT DOCUMENTS

| GB | 925048 A | 5/1963 |
|---|---|---|
| WO | 2004/090512 A1 | 10/2004 |
| WO | 2009/027726 A1 | 3/2009 |
| WO | 2009/122207 A1 | 10/2009 |

OTHER PUBLICATIONS

Search Report for corresponding priority application No. GB 0915338.8, Nov. 17, 2009.

Chinese Office Action with English translation issued in the corresponding application CN 100037.

* cited by examiner

ANALYSIS DEVICE WITH TRANSDUCER STIFFENING ELEMENTS

This application is filed under 35 U.S.C. §371 as the U.S. National Stage of International Application PCT/GB2010/051436, filed Sep. 1, 2010, which claims priority of the United Kingdom Patent Application No. 0915338.8, filed on Sep. 3, 2009 and U.S. Provisional Patent Application No. 61/239,976, filed on Sep. 4, 2009, the contents of which are hereby incorporated by reference in their entirety.

FIELD OF THE INVENTION

This invention relates to an analysis device comprising a pyroelectric or piezoelectric transducer or sensor. Such a device may, for example, be used to perform in vitro diagnosis (IVD) of a variety of medical conditions or diseases. More particularly, though not exclusively, the invention relates to such a device utilising a reagent which undergoes a colour change in the presence of an analyte, the change being detected by irradiating the reagent with electromagnetic radiation of an appropriate wavelength and then detecting absorption of the radiation as microscopic heating of the transducer. The invention also relates to such a device in which the migration of a coloured species towards the transducer can be detected by analysing the time delay between the irradiation of a sample and the subsequent microscopic heating of the transducer.

The invention also relates to a method of manufacturing an analysis device having a pyroelectric or piezoelectric transducer.

BACKGROUND TO THE INVENTION

A wide variety of diagnostic and other biochemical tests employ a reagent which undergoes a detectable colour change in the presence of the analyte. The reagent is often conveniently carried on a test strip. Optics may be provided to assist the comparison of the observed colour change with a standard colour chart. Alternatively, optical absorption may be measured at one or more selected wavelengths.

For example, in the particular field of immunoassays, internal reflection spectroscopy is used. According to this technique, a thin layer of sample material is established on a surface of a transparent optical element and measurements are made of internal reflection of light at the interface with the sample.

A drawback of many known analysis techniques is that they rely upon optical detection of emitted, reflected or transmitted light or fluorescence with subsequent signal processing providing the required measure of absorption. This is believed to have hindered the development of an analysis apparatus which is sensitive, compact and rugged. Under certain circumstances, where for example the analyte is potentially toxic or poses a microbiological contamination or health risk, it is also desirable to have analytical apparatus of a form which is disposable after each analysis.

U.S. Pat. No. 5,622,868 discloses a biochemical analysis device comprising a pyroelectric transducer in a strip form. The transducer is provided with thin film electrodes and one or more reagents are deposited on the transducer surface. The reagent undergoes a colorimetric change when it comes into contact with the analyte being detected. The analysis device is then typically inserted into a testing apparatus and the reagent is illuminated by a light emitting diode providing light of a predetermined wavelength. Absorption of the light by the reagent is detected as microscopic heating at the surface of the transducer and the electrical signal output from the transducer is processed to derive the concentration of the analyte being detected. Piezoelectric transducers may also be employed by the analysis device.

WO 2004/090512 A1 discloses a similar analysis device in which the migration of a coloured species towards the transducer surface can be detected by analysing the time delay between the pulsed irradiation of a sample with electromagnetic radiation and the subsequent microscopic heating of the transducer caused by absorption of the radiation by the coloured species.

The biochemical analysis devices of U.S. Pat. No. 5,622,868 and WO 2004/090512 A1 avoid the need for complicated optical detection systems and signal processing electronics and can therefore be manufactured in a single use, disposable form. However, a significant problem associated with biochemical analysis devices which comprise pyroelectric and piezoelectric transducers is that the transducers are very sensitive to mechanical movement and vibration, which environmental effects tend to lead to a high level of noise in the electrical output signal.

There is therefore a need for an analysis device comprising a pyroelectric or piezoelectric transducer for which noise caused by environmental effects is reduced.

SUMMARY OF THE INVENTION

According to an aspect of the present invention, there is provided an analysis device for use with an external testing apparatus to detect the presence of an analyte in a test sample, the device comprising:

a transducer formed of a layer of pyroelectric or piezoelectric material sandwiched between first and second electrode layers, the transducer being arranged to produce an electrical voltage across the electrode layers in response to heating or straining of the pyroelectric or piezoelectric material layer; and first and second stiffening elements for the transducer, the transducer being sandwiched between the stiffening elements, each of the stiffening elements defining a planar surface for maintaining the transducer in a flat condition, wherein each of the stiffening elements exposes a portion of a respective electrode layer of the transducer for electrically connecting the transducer to the external testing apparatus, the exposed portions being laterally offset from each other such that the exposed portions are each supported across the whole of their area by the stiffening element on the opposite side of the transducer.

The inventors have discovered that, by sandwiching the pyroelectric or piezoelectric transducer between planar stiffening elements, the noise caused by environmental effects can be reduced. The inventors have further developed a particularly effective arrangement for supporting the transducer with the stiffening elements while at the same time enabling access to the electrode layers of the transducer for making electrical connections.

In known analysis devices having a transducer, a portion of the transducer is typically exposed so that spring contacts are able to resiliently bear against the opposite electrode layers. The inventors have found that such an arrangement, in which the unsupported transducer is gripped between facing spring contacts, can vibrate or even resonate, thereby causing high levels of noise. According to the invention, connecting portions of the transducer are laterally offset and are each supported on one side by a stiffening element, to thereby reduce noise.

The novel arrangement not only mechanically supports the transducer across electrical connection portions of the electrode layers, but also facilitates the making of the electrical connections at laterally offset positions. It has been found that each of these features leads to significantly reduced noise caused by environmental factors. Herein, the term "laterally" refers to directions parallel to the plane of the transducer.

In preferred embodiments, the exposed portions of the first and second electrode layers are defined by cut outs formed in the respective first and second stiffening elements. The cut outs may have any shape, but rectangular cut outs are generally preferred. The provision of the cut outs may enable the size of the exposed portions to be relatively small, thereby limiting the extent of the areas over which the transducer is only supported on one side. The cut outs may be provided at the edges of the stiffening elements.

The cut outs may be laterally spaced apart such that an area of the transducer between the cut outs is supported by both of the first and second stiffening elements. In this way, the mechanical stability of the transducer may be improved. The cut outs may be arranged along one straight edge of the transducer, which may for example be substantially rectangular in shape.

Preferably, the whole of the area of the transducer is supported by the stiffening elements. In other words, the device is preferably arranged such that, at any position, the transducer is supported by at least one of the stiffening elements. The stiffening elements are preferably attached to the transducer by an adhesive, such as a pressure sensitive adhesive. Alternatively or additionally, the stiffening elements and the transducer may be clamped together by a suitable clamping mechanism.

The pyroelectric or piezoelectric material layer of the transducer may comprise polyvinylidene fluoride (PVDF). When suitably poled, as is known in the art, PVDF has both pyroelectric and piezoelectric material properties.

The first and second electrode layers are formed of an electrically conductive material, preferably one which is substantially transparent to electromagnetic radiation of a specific wavelength. The electrode layers may be formed of indium tin oxide (ITO), for example. The combined thickness of the transducer may be in the range 10 μm to 200 μm, preferably in the range 20 μm to 120 μm, and more preferably in the range 25 μm to 75 μm.

The device may further comprise at least one reagent arranged in the proximity of the transducer, for example on the surface of the transducer. The device may also comprise a planar spacing element arranged between the transducer and the first stiffening element. In this case, the spacing element may be provided with at least one aperture defining an analytical chamber enabling access to the transducer surface and containing the reagent. The spacing element may be thinner than either of the first and second stiffening elements. For example, the thickness of each stiffening element may be in the range 0.1 mm to 10 mm, preferably in the range 0.2 mm to 1.0 mm. The thickness of the spacing element may be in the range 0.05 mm to 1.0 mm, preferably in the range 0.1 mm to 0.5 mm.

One or both of the first and second stiffening elements may be formed of a polymer material such as polymethyl methacrylate (PMMA). Other materials, including composites, may also be suitable, provided they are sufficiently rigid to provide some mechanical support to the transducer. The stiffening elements may be moulded or formed by other processes such as cutting out from a supply of sheet of material. Such processes are generally suitable provided the resulting stiffening elements have at least one flat surface for supporting the transducer. The stiffening elements are preferably substantially transparent to electromagnetic radiation.

In a preferred embodiment, the first stiffening element is an integral part of a main body formed of a moulded plastics material. The main body may define a recess, the transducer and the second stiffening element being arranged inside the recess such that the exposed portions of the first and second electrode layers of the transducer remain exposed. The main body may define fluidic channels for receiving the test sample. The main body may be formed of a polymer material such as polymethyl methacrylate.

According to another aspect of the present invention, there is provided a biochemical analysis system comprising: a biochemical analysis device comprising the analysis device described above; and a testing apparatus electrically connected to the exposed portions of the first and second electrode layers of the transducer, the testing apparatus having a microprocessor for processing electrical signals received from the first and second electrode layers.

According to yet another aspect of the present invention, there is provided a method of manufacturing an analysis device for use with an external testing apparatus to detect the presence of an analyte in a test sample, the method comprising:

forming a transducer by forming first and second electrode layers over opposite surfaces of a layer of pyroelectric or piezoelectric material, the transducer being arranged to produce an electrical voltage across the electrode layers in response to heating or straining of the pyroelectric or piezoelectric material layer; and providing first and second stiffening elements over respective electrode layers of the transducer, each of the stiffening elements defining a planar surface for maintaining the transducer in a flat condition, wherein the stiffening elements are arranged such that each of the stiffening elements exposes a portion of a respective electrode layer of the transducer for electrically connecting the transducer to the external testing apparatus, the exposed portions being laterally offset from each other such that the exposed portions are each supported across the whole of their area by the stiffening element on the opposite side of the transducer.

The step of forming the transducer preferably comprises poling the pyroelectric or piezoelectric material layer, before the electrode layers are formed.

Further features and advantages will be apparent from the detailed description of the present invention provided hereinbelow.

BRIEF DESCRIPTION OF THE DRAWINGS

Specific embodiments of the present invention will now be described with reference to the accompanying drawings, in which.

DETAILED DESCRIPTION

The present invention provides an analysis device which is intended to be used with an external testing apparatus to detect the presence of an analyte in a test sample. The device comprises a transducer formed of a layer of pyroelectric or piezoelectric material sandwiched between first and second electrode layers. The transducer is arranged to produce an electrical voltage across the electrode layers in response to heating or straining of the pyroelectric or piezoelectric material layer. The device also comprises first and second stiffening elements the transducer, the transducer being sandwiched between the stiffening elements. Each of the stiffening elements defines a planar surface for maintaining the transducer in a flat condition.

According to the present invention, each of the stiffening elements exposes a portion of a respective electrode layer of the transducer for electrically connecting the transducer to the external testing apparatus. The exposed portions of the electrode layers are laterally offset from each other such that the exposed portions are each supported across the whole of their area by the stiffening element on the opposite side of the transducer.

A preferred embodiment of the present invention is based on the known biochemical analysis systems of the type disclosed in U.S. Pat. No. 5,622,868 and WO 2004/090512 A1. The known systems employ reagents which undergo a detectable colour change and/or cause migration of a coloured species towards the transducer to provide an indication of an analyte in a biological fluid sample. The systems may be arranged to detect a colour change by irradiating the reagent with electromagnetic radiation of an appropriate wavelength, and then detecting absorption of the radiation as microscopic heating of a pyroelectric transducer arranged in the vicinity of the reagent. The systems may be arranged to detect the migration of a coloured species towards the transducer by analysing the time delay between the irradiation of the sample and the subsequent microscopic heating of the transducer.

Figure 1:
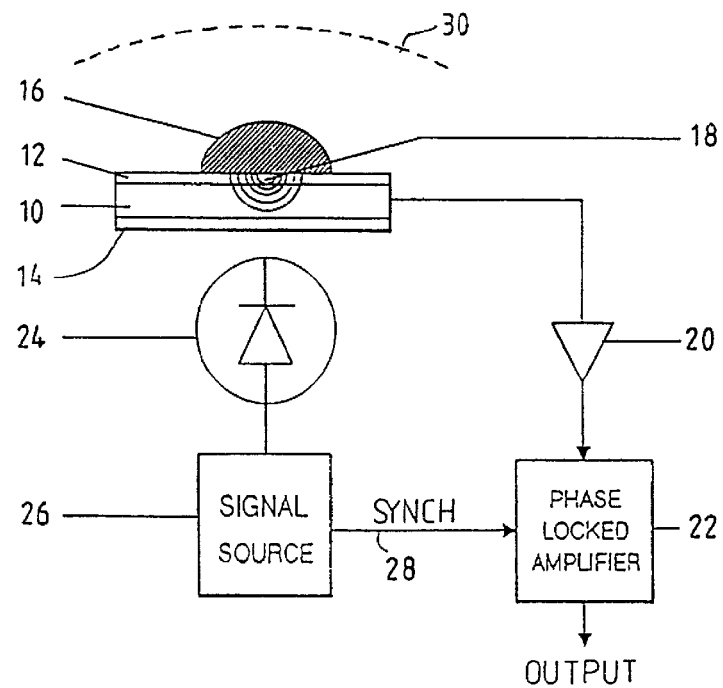
FIG. 1 is a schematic view of a known analytical system.

FIG. 1 is a schematic view of the known system, which includes an analysis device carrying the pyroelectric transducer. Referring to the figure, the transducer includes a PVDF film 10 having electrode coatings 12, 14 on the upper and lower surfaces respectively. The electrode coatings are formed of indium tin oxide (ITO) having a thickness in the range 5 nm to 100 nm. Strips of reagent 16 are deposited, using any suitable technique, upon the upper electrode coating 12 of the transducer.

The electrode coatings 12 and 14 are connected, via exposed electrical connectors on the analysis device, to an external testing apparatus. The connectors (not shown) are coupled to the inputs of a charge amplifier 20 presenting a high input impedance, and the output of the charge amplifier is taken to a phase locked amplifier 22. A light source 24 of the testing apparatus, in the form of a light emitting diode (LED), is positioned so as to illuminate the reagent strips through the pyroelectric film 10 and its associated electrode coatings. The light source is powered through a modulator 26 which provides a square wave output typically up to about 15 Hz. A reference signal is taken on line 28 from the modulator 26 to the phase locked amplifier 22.

In use of the known system, a biological fluid sample is collected and deposited upon the upper surface of the pyroelectric transducer of the analysis device, the outline of the drop being shown in the drawing at 30. In the presence of levels of the analyte, the appropriately chosen reagent undergoes a change in optical absorption or a coloured species migrates towards the surface of the transducer. Light of an appropriate wavelength from the source 24 is absorbed in the reagent, causing microscopic heating over a localised region 18. This heating is sensed by the transducer and results in a change in output from the amplifier 20. Through phase locking on the reference signal on line 28, the amplifier 22 is able to provide a sensitive output signal indicative of the heating and thus of the light absorption within the reagent and presence of the analyte within the biological fluid sample. The output of phase locked amplifier 22 is digitised and sent on an appropriate bus to a microprocessor.

The type of reagent chosen will vary widely depending upon the analytical procedure. For example, in tests for ions, pH and heavy metal indicator dyes may be employed which change colour on chelation/binding of ions. A variety of reagents are known for assays of metabolites, drugs and biochemicals in blood and urine. One example is a paracetamol assay with production of aminophenol from paracetamol by arylacylamidase. In immunological assays, the reagent may take the form of a protein or microbial antigen. The reagent may also be the antibody. The technique is also applicable to enzyme linked immunosorbent assays (ELISA).

Figure 2:
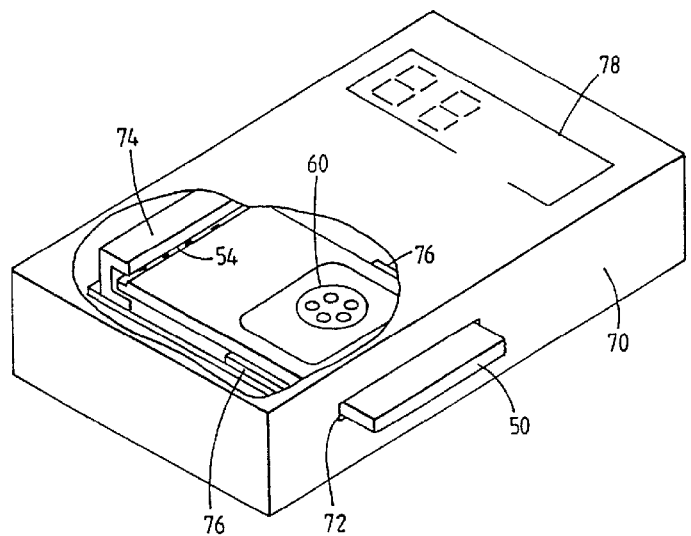
FIG. 2 illustrates a testing apparatus and test element embodying the known system shown in FIG. 1.

FIG. 2 illustrates a remote testing apparatus 70 and analysis device 50 embodying the known system shown in FIG. 1. The analysis device 50 is in the form of a single use cartridge, thereby removing the problems of contamination and of cleaning potentially hazardous sample material. The analysis device 50 comprises an inert transparent substrate of rectangular form. At one end, the substrate is provided with electrical connectors 54 enabling the test element to be plugged into the testing apparatus 70. The substrate carries the pyroelectric transducer comprising the PVDF film 10 having electrode coatings 12, 14. A well 60 is defined on the surface of the transducer for receiving the biological fluid sample.

With further reference to FIG. 2, the testing apparatus 70 comprises a housing provided with a slot 72 into which the analysis device 50 can be slidingly engaged. Internally, the housing provides an edge connector 74 designed to mate with the electrical connectors 54 on the analysis device 50. A light source shown schematically at 76 is positioned within the housing 70 so as to be aligned with the well 60 when the analysis device 50 is fully engaged.

The testing apparatus 70 contains circuitry (not shown) providing the modulated signal source, charge amplifier and phase locked amplifier as described hereinabove with reference to FIG. 1. There is further provided a microprocessor, which may be of commercially available form, which is connected to receive the output of the phase locked amplifier and to control a display 78.

The present invention is based on the known analysis device described hereinabove, but has a novel arrangement which reduces noise caused by environmental effects.

Figure 3:
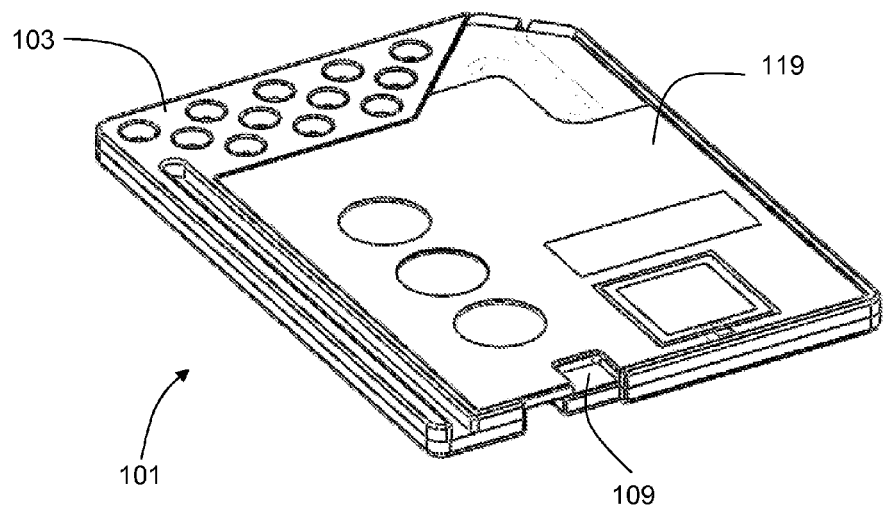
FIG. 3 is a perspective view of an analysis device according to the present invention.
Figure 4:
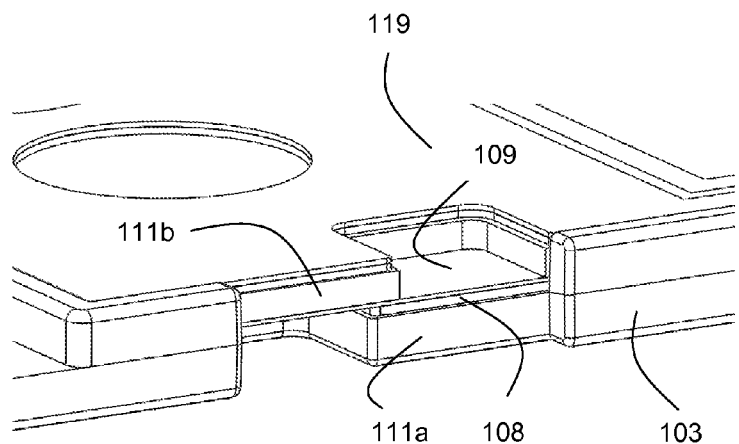
FIG. 4 is a perspective view showing elements of the analysis device shown in FIG. 3 in greater detail.
Figure 5:
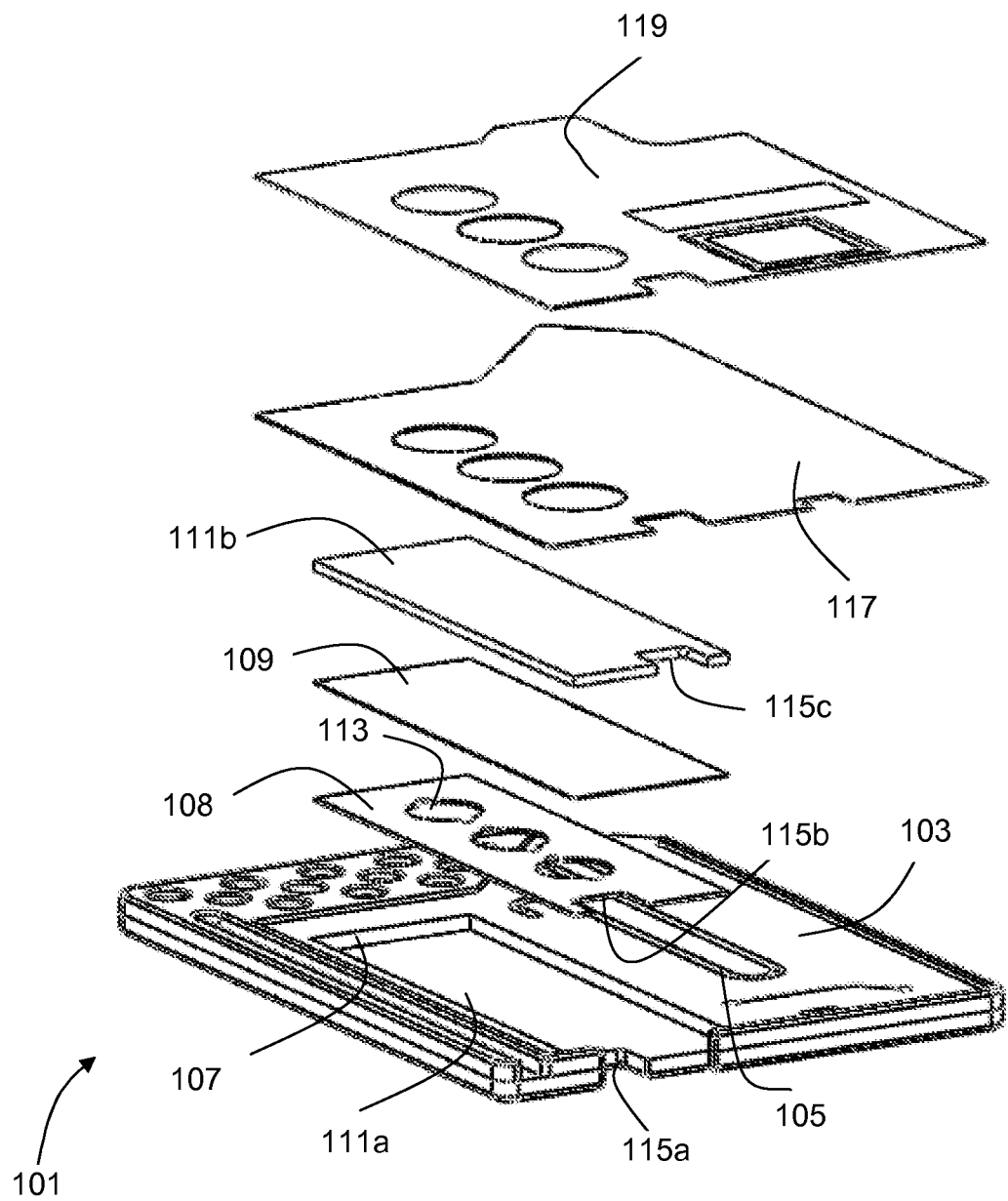
FIG. 5 is an exploded view of the analysis device shown in FIG. 3.

FIG. 3 is a perspective view of a biochemical analysis device according to the present invention. FIG. 4 is an enlarged view of the device shown in FIG. 3. FIG. 5 is an exploded view of the device shown in FIG. 3 showing its main component parts more clearly.

With reference to the figures, the biochemical analysis device 101 according to the present invention is provided as a single use, disposable cartridge. The outer shape of the analytical device 101 is defined by a transparent main body 103 moulded from polymethyl methacrylate. The main body 103 is provided with fluidic passages 105 arranged to receive a sample of a biological fluid such as whole blood, serum, plasma or urine, and a port (not shown) arranged to receive a source of vacuum to draw the sample through the fluidic passages 105. The main body 103 also defines a rectangular recess 107 in its upper surface for receiving a transducer assembly. The base of the recess 107 forms a first (lower) stiffening element 111a.

The transducer assembly comprises a transducer 109 arranged between a planar spacing element 108 and a second (upper) stiffening element 111b.

The transducer 109 is formed of two thin films of pyroelectric material in the form of polyvinylidene fluoride sandwiched between first (lower) and second (upper) electrode layers. The pyroelectric films are poled according to a technique well known in the art, and are arranged such that their polarities are reversed for providing common-mode noise rejection. The electrode layers are formed of indium tin oxide (ITO).

The transducer 109 has a rectangular outer shape, with the pyroelectric films and the electrode layers being coextensive. The combined thickness of the transducer 109 is approximately 70 μm, with each of the electrode layers accounting for approximately 35 nm of thickness. The transducer 109 is formed to be transparent to electromagnetic radiation of a specific wavelength. The transducer 109, constructed in this way, is able to produce an electrical voltage across the electrode layers in response to microscopic heating of one of the pyroelectric films.

The stiffening elements 111a, 111b are formed as thin but rigid layers of polymethyl methacrylate (acrylic) having planar (flat) surfaces facing the transducer 109. The first stiffening element 111a is integrally formed with the main body 103 and has a thickness of approximately 1.5 mm. The second stiffening element 111b, which is a separate component, has a thickness of approximately 0.75 mm.

The planar spacing element 108 arranged between the first stiffening element 111a and the transducer 109 is provided with three apertures 113 and has a thickness of approximately 0.25 mm. The apertures 113 of the spacing element 111a define analytical chambers which expose the surface of the transducer 109 and within which are disposed suitable reagents (not shown).

The stiffening elements 111a, 111b have an outer shape and size (length and width) that are identical to those of the transducer 109, except that the edge of each stiffening element 111a, 111b is provided with a small cut out 115a, 115c exposing the surface of a respective electrode layer of the transducer 109. The cut outs 115a, 115c are provided along corresponding edges of the stiffening elements 111a, 111b and are laterally spaced apart form each other. The cut outs 115a, 115c have a shape which is substantially rectangular.

The spacing element 108 has an outer shape and size (length and width) that is identical to those of the first stiffening element 111a, and includes a cut out 115b in registration with the cut out 115a of the first stiffening element 111a.

The cut outs 115a, 115c of the stiffening elements and the cut out 115b of the spacing element enable access to the electrode layers of the transducer 109 for electrically connecting the transducer 109 to the external testing apparatus (not shown).

When the transducer assembly is received into the recess 107 formed in the main body 103, the upper surface of the transducer assembly lies flush with the upper surface of the main body 103. The first stiffening element 111a and the components of the transducer assembly are attached to each other across their area by a pressure sensitive adhesive.

The analytical device 101 further comprises an upper seal 117, which is attached to the main body 103 with an adhesive. A paper label 119 is applied over the upper seal 117 and may be provided with product information, instructions or regulatory data for the device 101. The paper label 119 and the upper seal 117 are provided with windows in registration with the analytical chambers 113 and cut outs in registration with the cut out 115c formed in the second stiffening element 111b.

In use of the device 101 to sample and test whole blood, the skin on the tip of a patient's finger is pierced and a collection end of the fluidic passage 105 is presented to the blood so elicited. The blood is then drawn into the fluidic passage 105 by capillary action.

To perform an analysis, the analytical device 101 containing the collected blood sample is inserted into the external testing apparatus (not shown), thereby causing electrical contacts arranged inside the testing apparatus engage the exposed portions of the electrode layers of the transducer 109. By reason of the unique arrangement of the analytical device, the exposed portions of the electrode layers are supported from the opposite side by the stiffening elements 111a, 111b.

The blood sample is then drawn through the fluidic channels 105 by applying a vacuum source to a port formed in the main body 103 or applying a positive pressure to the collection end of the fluidic passage 105. The blood sample is received into the analytical chambers 113 whereupon it comes into contact with the reagents, which undergo a detectable colour change or which cause migration of a coloured species towards the surface of the transducer 109 to provide an indication of an analyte in a biological fluid sample. The colour change or migration is detected by irradiating the reagents with electromagnetic radiation of an appropriate wavelength, and then detecting absorption of the radiation as microscopic heating of the pyroelectric transducer 109.

As described above, the unique arrangement of the analytical device 101, and particularly the way in which electrical connection of the transducer 109 to the external testing apparatus is facilitated, provides a significant reduction in electrical noise compared to known devices.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An analysis device for use with an external testing apparatus to detect the presence of an analyte in a test sample, the device comprising:
   a transducer formed of a layer of pyroelectric or piezoelectric material sandwiched between first and second electrode layers, the transducer being arranged to produce an electrical voltage across the electrode layers in response to heating or straining of the pyroelectric or piezoelectric material layer; and
   first and second stiffening elements for the transducer, the transducer being sandwiched between the stiffening elements, each of the stiffening elements defining a planar surface for maintaining the transducer in a flat condition, wherein each of the stiffening elements exposes a portion of a respective electrode layer of the transducer for electrically connecting the transducer to the external testing apparatus, the exposed portions being laterally offset from each other such that the exposed portions are each supported across the whole of their area by the stiffening element on the opposite side of the transducer.

2. An analysis device as claimed in claim 1, wherein the exposed portions of the first and second electrode layers are defined by cut outs in the respective first and second stiffening elements.

3. An analysis device as claimed in claim 2, wherein the cut outs are laterally spaced apart such that an area of the transducer between the cut outs is supported by both of the first and second stiffening elements.

4. An analysis device as claimed in claim 2, wherein the cut outs are arranged along one straight edge of the transducer.

5. An analysis device as claimed in claim 1, wherein the transducer and at least one of the stiffening elements are rectangular in shape.

6. An analysis device as claimed in claim 1, wherein the whole of the area of the transducer is supported by at least one of the stiffening elements.

7. An analysis device as claimed in claim 1, wherein the pyroelectric or piezoelectric material layer of the transducer comprises polyvinylidene fluoride (PVDF).

8. An analysis device as claimed in claim 1, wherein at least one of the first and second electrode layers of the transducer covers at least 90% of the area of the pyroelectric or piezoelectric material layer.

9. An analysis device as claimed in claim 1, wherein the first and second electrode layers are formed of indium tin oxide (ITO).

10. An analysis device as claimed in claim 1, further comprising at least one reagent arranged in the proximity of the transducer.

11. An analysis device as claimed in claim 10, further comprising a spacing element arranged between the transducer and the first stiffening element, and wherein the spacing element is provided with at least one aperture defining an analytical chamber, the at least one reagent being provided therein.

12. An analysis device as claimed in claim 11, wherein the spacing element is thinner than either of the first and second stiffening elements.

13. An analysis device as claimed in claim 1, wherein at least one of the first and second stiffening elements is formed of polymethyl methacrylate (PMMA).

14. An analysis device as claimed in claim 1, wherein the first stiffening element is part of a main body, the main body defining a recess, the transducer and the second stiffening element being arranged inside the recess such that the exposed portions of the first and second electrode layers of the transducer remain exposed.

15. An analysis device as claimed in claim 14, wherein the main body defines fluidic channels for receiving the test sample.

16. An analysis device as claimed in claim 1, wherein the first and second stiffening elements are adhered to the transducer.

17. A biochemical analysis device comprising an analysis device for use with an external testing apparatus to detect the presence of an analyte in a test sample, the analysis device comprising:
a transducer formed of a layer of pyroelectric or piezoelectric material sandwiched between first and second electrode layers, the transducer being arranged to produce an electrical voltage across the electrode layers in response to heating or straining of the pyroelectric or piezoelectric material layer; and
first and second stiffening elements for the transducer, the transducer being sandwiched between the stiffening elements, each of the stiffening elements defining a planar surface for maintaining the transducer in a flat condition,
wherein each of the stiffening elements exposes a portion of a respective electrode layer of the transducer for electrically connecting the transducer to the external testing apparatus, the exposed portions being laterally offset from each other such that the exposed portions are each supported across the whole of their area by the stiffening element on the opposite side of the transducer.

18. A biochemical analysis system comprising:
a biochemical analysis device for use with an external testing apparatus to detect the presence of an analyte in a test sample, the analysis device comprising:
a transducer formed of a layer of pyroelectric or piezoelectric material sandwiched between first and second electrode layers, the transducer being arranged to produce an electrical voltage across the electrode layers in response to heating or straining of the pyroelectric or piezoelectric material layer; and
first and second stiffening elements for the transducer, the transducer being sandwiched between the stiffening elements, each of the stiffening elements defining a planar surface for maintaining the transducer in a flat condition,
wherein each of the stiffening elements exposes a portion of a respective electrode layer of the transducer for electrically connecting the transducer to the external testing apparatus, the exposed portions being laterally offset from each other such that the exposed portions are each supported across the whole of their area by the stiffening element on the opposite side of the transducer; and
a testing apparatus electrically connected to the exposed portions of the first and second electrode layers of the transducer, the testing apparatus having a microprocessor for processing electrical signals received from the first and second electrode layers.

19. A method of manufacturing an analysis device for use with an external testing apparatus to detect the presence of an analyte in a test sample, the method comprising:
forming a transducer by forming first and second electrode layers over opposite surfaces of a layer of pyroelectric or piezoelectric material, the transducer being arranged to produce an electrical voltage across the electrode layers in response to heating or straining of the pyroelectric or piezoelectric material layer; and
providing first and second stiffening elements over respective electrode layers of the transducer, each of the stiffening elements defining a planar surface for maintaining the transducer in a flat condition,
wherein the stiffening elements are arranged such that each of the stiffening elements exposes a portion of a respective electrode layer of the transducer for electrically connecting the transducer to the external testing apparatus, the exposed portions being laterally offset from each other such that the exposed portions are each supported across the whole of their area by the stiffening element on the opposite side of the transducer.

20. A method as claimed in claim 19, wherein the step of forming the transducer comprises poling the pyroelectric or piezoelectric material layer prior to forming the electrode layers.

* * * * *

UNITED STATES PATENT AND TRADEMARK OFFICE
CERTIFICATE OF CORRECTION

PATENT NO. : 9,068,930 B2  
APPLICATION NO. : 13/394090  
DATED : June 30, 2015  
INVENTOR(S) : Paul Brendan Monaghan et al.

Page 1 of 1

It is certified that error appears in the above-identified patent and that said Letters Patent is hereby corrected as shown below:

Title page, item (75) inventors: "Timothy Joseph Nicholas Carter, Sheemess (GB)" should be
--Timothy Joseph Nicholas Carter, Sheerness (GB)--

Signed and Sealed this
Twelfth Day of April, 2016

Michelle K. Lee
*Director of the United States Patent and Trademark Office*